United States Patent
Zubizarreta et al.

(10) Patent No.: US 11,553,928 B2
(45) Date of Patent: Jan. 17, 2023

(54) TIBIAL CUTTING GUIDE ASSEMBLIES AND ASSOCIATED INSTRUMENTATION FOR PERFORMING SURGICAL METHODS

(71) Applicant: ARTHREX, INC., Naples, FL (US)

(72) Inventors: Joel Zubizarreta, Naples, FL (US); Alex Bautsch, Naples, FL (US)

(73) Assignee: ARTHREX, INC., Naples, FL (US)

( * ) Notice: Subject to any disclaimer, the term of this patent is extended or adjusted under 35 U.S.C. 154(b) by 62 days.

(21) Appl. No.: 17/116,489

(22) Filed: Dec. 9, 2020

(65) Prior Publication Data

US 2022/0175397 A1 Jun. 9, 2022

(51) Int. Cl.
| | |
|---|---|
| A61B 17/58 | (2006.01) |
| A61B 17/60 | (2006.01) |
| A61F 2/00 | (2006.01) |
| A61B 17/15 | (2006.01) |
| A61B 17/17 | (2006.01) |
| A61B 17/56 | (2006.01) |
| A61B 17/68 | (2006.01) |

(52) U.S. Cl.
CPC ........ *A61B 17/157* (2013.01); *A61B 17/1764* (2013.01); *A61B 2017/564* (2013.01); *A61B 2017/681* (2013.01)

(58) Field of Classification Search
CPC combination set(s) only.
See application file for complete search history.

(56) References Cited

U.S. PATENT DOCUMENTS

| | | | |
|---|---|---|---|
| 4,759,350 A | 7/1988 | Dunn et al. | |
| 5,129,909 A | 7/1992 | Sutherland | |
| 5,980,526 A | 11/1999 | Johnson et al. | |
| 8,167,888 B2 | 5/2012 | Steffensmeier | |
| 8,425,523 B2 | 4/2013 | Aram et al. | |
| 8,911,444 B2 | 12/2014 | Bailey | |
| 9,138,237 B2 | 9/2015 | Meade et al. | |
| 9,237,952 B2 | 1/2016 | Kurtz | |
| 9,974,550 B2 | 5/2018 | Seitlinger et al. | |
| 2003/0130665 A1* | 7/2003 | Pinczewski | A61B 17/154 606/88 |
| 2005/0203528 A1 | 9/2005 | Couture et al. | |
| 2010/0168753 A1 | 7/2010 | Edwards et al. | |
| 2014/0364857 A1 | 12/2014 | Bojarski et al. | |
| 2018/0000497 A1 | 1/2018 | Park et al. | |

FOREIGN PATENT DOCUMENTS

| | | |
|---|---|---|
| KR | 101273262 B1 | 6/2013 |
| WO | 2010/029333 A1 | 3/2010 |

OTHER PUBLICATIONS

International Search Report and Written Opinion for International application No. PCT/US2021/062385 dated Feb. 23, 2022.

* cited by examiner

*Primary Examiner* — Sameh R Boles

(74) *Attorney, Agent, or Firm* — Carlson, Gaskey & Olds, P.C.

(57) ABSTRACT

This disclosure is directed to tibial cutting guide assemblies for preparing a tibia for receiving an arthroplasty implant. Exemplary tibial cutting guide assemblies may include a tibial cutting block for making precise cuts in the tibia, and a slope setting pin for establishing a patient specific tibial slope. The tibial cutting guide assemblies allow for level resection while providing surgical control over internal/external rotation and varus/valgus alignment.

12 Claims, 10 Drawing Sheets

TIBIAL CUTTING GUIDE ASSEMBLIES AND ASSOCIATED INSTRUMENTATION FOR PERFORMING SURGICAL METHODS

BACKGROUND

This disclosure relates to surgical devices, and more particularly to orthopedic surgical devices for performing arthroplasties.

Arthroplasty is an orthopedic surgical procedure performed to repair or replace diseased joints. For example, total knee arthroplasty (TKA) may be performed to treat patients with diseased knee joints. Specific tools and instruments are required for preparing knee bones for receiving arthroplasty implants.

SUMMARY

A tibial cutting guide assembly according to an exemplary aspect of the present disclosure includes, among other things, a tibial cutting block including a biasing clip, and a slope setting pin biased toward a surface of the tibial cutting block by the biasing clip.

In a further non-limiting embodiment of the foregoing tibial cutting guide assembly, the slope setting pin is adjustably received within a pin receiving slot of the tibial cutting block.

In a further non-limiting embodiment of either of the foregoing tibial cutting guide assemblies, the surface is an upper wall of a block body of the tibial cutting block that delineates a portion of the pin receiving slot.

In a further non-limiting embodiment of any of the foregoing tibial cutting guide assemblies, a block body of the tibial cutting block includes a unitary, monoblock design and is made of a polymeric material.

In a further non-limiting embodiment of any of the foregoing tibial cutting guide assemblies, the tibial cutting block includes a first cutting slot and a second cutting slot that is separated from the first cutting slot by an interior wall of the tibial cutting block.

In a further non-limiting embodiment of any of the foregoing tibial cutting guide assemblies, a first fixation pin hole and a second fixation pin hole extend through the tibial cutting block and open into the first cutting slot.

In a further non-limiting embodiment of any of the foregoing tibial cutting guide assemblies, a third fixation pin hole extends through the tibial cutting block and opens into the second cutting slot.

In a further non-limiting embodiment of any of the foregoing tibial cutting guide assemblies, the biasing clip includes a first end portion integrally formed with an inner wall of a front side of the tibial cutting block, a second end portion arranged adjacent to an inner wall of a tibial attachment side of the tibial cutting block, and an arced curvature between the first end portion and the second end portion.

In a further non-limiting embodiment of any of the foregoing tibial cutting guide assemblies, the biasing clip establishes a floor of a pin receiving slot of the tibial cutting block, and further wherein the slope setting pin is movably received within the pin receiving slot.

In a further non-limiting embodiment of any of the foregoing tibial cutting guide assemblies, the slope setting pin includes an elongated shaft including a distal section that includes a hook-shaped tip and a pair of flat surfaces.

In a further non-limiting embodiment of any of the foregoing tibial cutting guide assemblies, the slope setting pin includes an elongated shaft including a proximal section, a distal section, and a mid-section. The proximal section includes a first diameter that is smaller than a second diameter of the mid-section.

An arthroplasty instrument set according to another exemplary aspect of the present disclosure includes, among other things, a tibial cutting block assembly, a varus-valgus alignment device, and at least two fixation pins.

A method of preparing a bone for receiving an arthroplasty implant includes, among other things, positioning a slope setting pin of a tibial cutting guide assembly within a joint space between a femur and a tibia, securing a tibial cutting block of the tibial cutting guide assembly to the tibia with a first fixation pin, bending a portion of the slope setting pin away from the tibial cutting block, inserting a second fixation pin through the tibial cutting block, and making a first cut in the tibia through a first cutting slot of the tibial cutting block.

In a further non-limiting embodiment of the foregoing method, positioning the slope setting pin includes positioning a hook-shaped tip of the slope setting pin against a posterior surface of the tibia.

In a further non-limiting embodiment of either of the foregoing methods, prior to bending the portion of the slop setting pin, the method includes inserting a third fixation pin through the tibial cutting block.

In a further non-limiting embodiment of any of the foregoing methods, bending the portion of the slope setting pin includes bending a proximal section of an elongated shaft of the slope setting pin, thereby altering a position of a handle of the slope setting pin relative to the tibial cutting block.

In a further non-limiting embodiment of any of the foregoing methods, prior to bending the portion of the slop setting pin, the method includes inserting a drop rod of a varus-valgus alignment device through the tibial cutting block and adjusting a varus-valgus alignment of the tibial cutting block relative to the tibia via the drop rod.

In a further non-limiting embodiment of any of the foregoing methods, the method includes making a second cut in the tibia through a second cutting slot of the tibial cutting block.

In a further non-limiting embodiment of any of the foregoing methods, the slope setting pin establishes a patient specific tibial slope when positioned in the joint space.

In a further non-limiting embodiment of any of the foregoing methods, the slope setting pin is biased against a surface of the tibial cutting block by a biasing clip of the tibial cutting block.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure is directed to tibial cutting guide assemblies for preparing a tibia for receiving an arthroplasty implant. Exemplary tibial cutting guide assemblies may include a tibial cutting block for making precise cuts in the tibia, and a slope setting pin for establishing a patient specific tibial slope. The tibial cutting guide assemblies allow for a level resection while providing surgical control over internal/external rotation and varus/valgus alignment. These and other features of this disclosure are discussed in greater detail in the following paragraphs of this detailed description.

Figure 1:
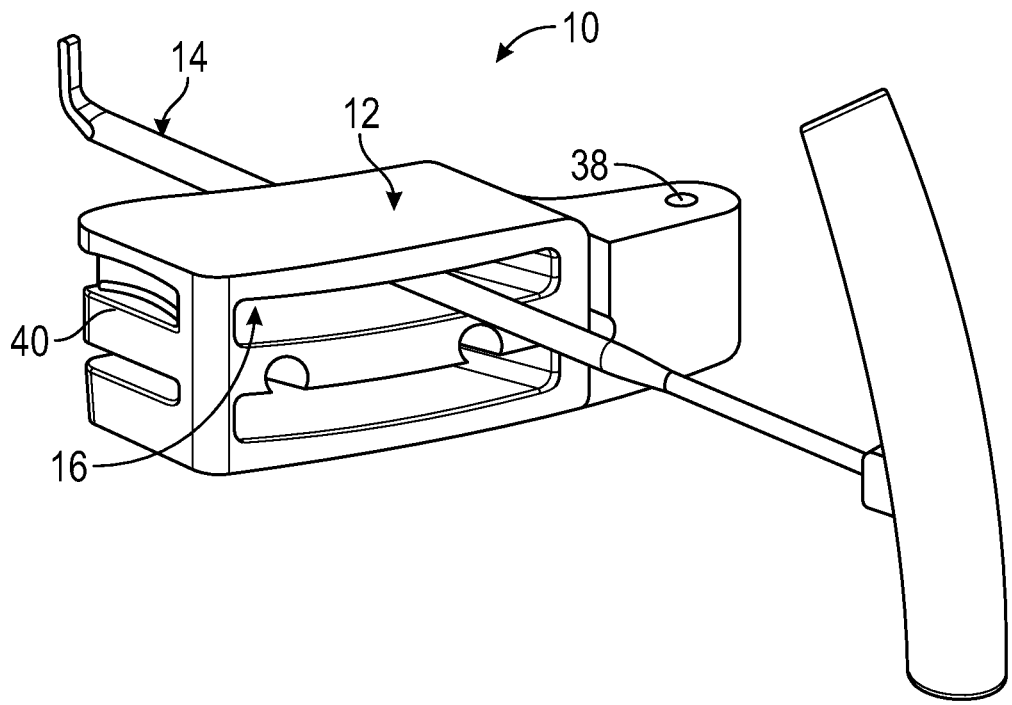
FIG. 1 illustrates an exemplary tibial cutting guide assembly of an arthroplasty instrument set.
Figure 2:
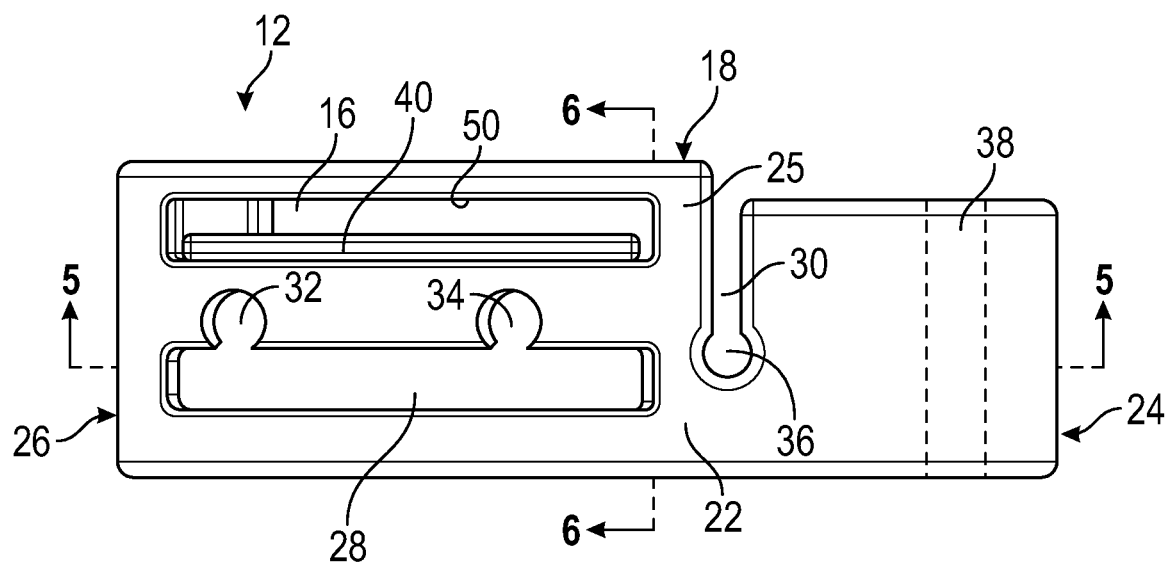
FIG. 2 is a front view of a tibial cutting block of the tibial cutting guide assembly of FIG. 1.
Figure 3:
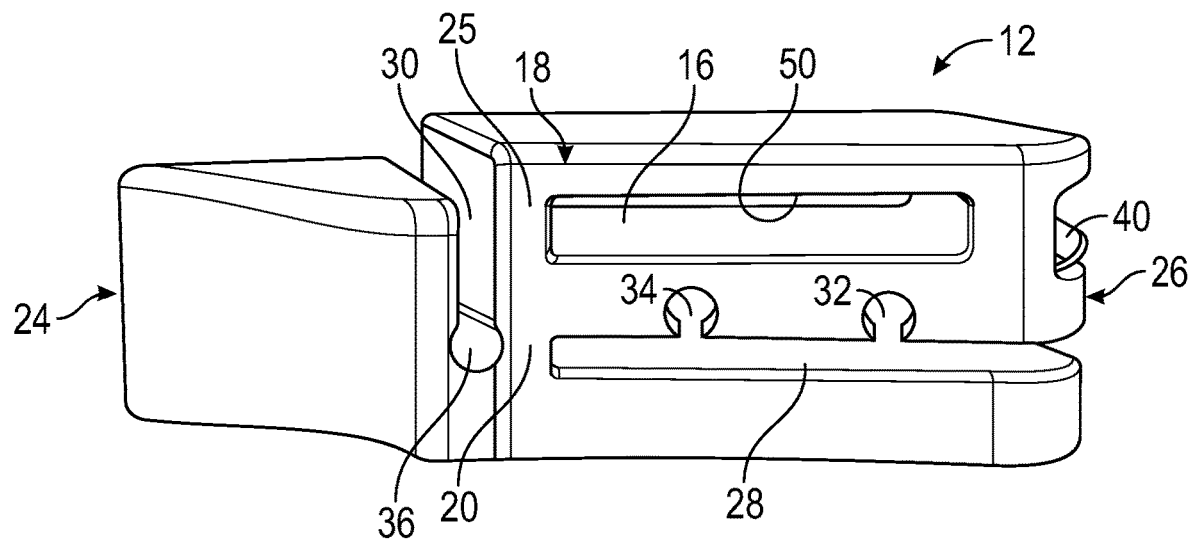
FIG. 3 is a rear view of the tibial cutting block of FIG. 2.

FIG. 1 illustrates a tibial cutting guide assembly 10 that may be used to prepare a patient for the implantation of an arthroplasty implant, such as during an arthroplasty procedure. In an embodiment, the tibial cutting guide assembly 10 is part of an arthroplasty instrument set that may be used to prepare a patient's tibia and femur, such as by sizing, marking, and making numerous cuts in the tibia and the femur, for preparing the knee joint for the implantation of one or more knee arthroplasty implants. However, the illustrated instruments are not limited to uses associated with the tibia and femur and could have additional applications for preparing for the implantation of any total joint implant.

The tibial cutting guide assembly 10 may include a tibial cutting block 12 and a slope setting pin 14. As further discussed below, the tibial cutting block 12 may be used for making precise cuts in a patient's tibia, and the slope setting pin 14 may be movably received within a pin receiving slot 16 of the tibial cutting block 12 for establishing a patient specific tibial slope. The tibial cutting guide assembly 10 may further provide for a level resection of the tibia while facilitating surgical control over internal/external rotation and varus/valgus alignment.

The tibial cutting block 12 of the tibial cutting guide assembly 10 of FIG. 1 is further illustrated with reference to FIGS. 2-6. The tibial cutting block 12 may include a block body 18 having a unitary, monoblock design that includes a tibial attachment side 20, a front side 22 opposed to the tibial attachment side 20, a right side 24, and a left side 26. In this embodiment, the right side 24 is oriented to the cruciate ligament while the left side 26 is oriented either medially or laterally. Therefore, the tibial cutting block 12 may be used medially at the left tibia or laterally at the right tibia. A tibial cutting block for use laterally at the left tibia or medially at the right tibia would be oriented as the mirror image of the tibial cutting block 12 shown in FIGS. 2-6.

The tibial attachment side 20 of the block body 18 may include a slightly arced curvature that mimics the curvature of the anterior surface of the proximal tibia. The front side 22 of the block body 18 may also be slightly curved to facilitate handling of the tibial cutting block 12.

The pin receiving slot 16, a first cutting slot 28, a second cutting slot 30, a first fixation pin hole 32, a second fixation pin hole 34, and a third fixation pin hole 36 may be formed through the block body 18 and may extend in an anterior-posterior direction for penetrating through both the tibial attachment side 20 and the front side 22. The pin receiving slot 16 has a length in the left-right direction (relative to a patient) and is configured to receive the slope setting pin 14. In an embodiment, the pin receiving slot 16 is located superior to, or vertically above, the first cutting slot 28.

The first cutting slot 28 has a length in the left-right direction and is configured as a capture for guiding a saw blade or other cutting tool through the block body 18 for making horizontal cuts in a tibia. The second cutting slot 30 has a length in the superior-inferior direction and is configured as another capture for guiding a saw blade or other cutting tool through the block body 18 for making vertical cuts in the tibia. In an embodiment, the second cutting slot 30 is located axially between the first cutting slot 28 and the right side 24 of the block body 18. An interior wall 25 of the block body 18 separates the second cutting slot 30 from the first cutting slot 28 such that these slots do not intersect one another.

The first fixation pin hole 32, the second fixation pin hole 34, and the third fixation pin hole 36 may establish anterior-posterior oriented channels through the block body 18 and are each configured to allow for the insertion of a fixation pin (not shown in FIGS. 2-6) for temporarily fixating the tibial cutting block 12 to the tibia. The first and second fixation pin holes 32, 34 may be positioned just above (i.e., superior to) the first cutting slot 28 and may open into the first cutting slot 28. The third fixation pin hole 36 may be positioned just below (i.e., inferior to) the second cutting slot 30 and may open into the second cutting slot 30.

The first and second fixation pin holes 32, 34 may converge toward one another at an angle a (see FIG. 5) in the anterior-to-posterior direction. In an embodiment, the angle α is between 10 and 30 degrees. In another embodiment, the angle α is between 15 and 25 degrees. In yet another embodiment, the angle α is about 15 degrees. The angle α is designed help prevent the tibial cutting block 12 from being pulled away from the tibia during use.

An alignment rod hole 38 (best shown in FIGS. 2 and 5) may be formed through the right side 24 of the block body 18. The alignment rod hole 38 may include a length extending in the superior-inferior direction and is configured to receive a varus-valgus alignment device (not shown in FIGS. 2-6).

Figure 4:
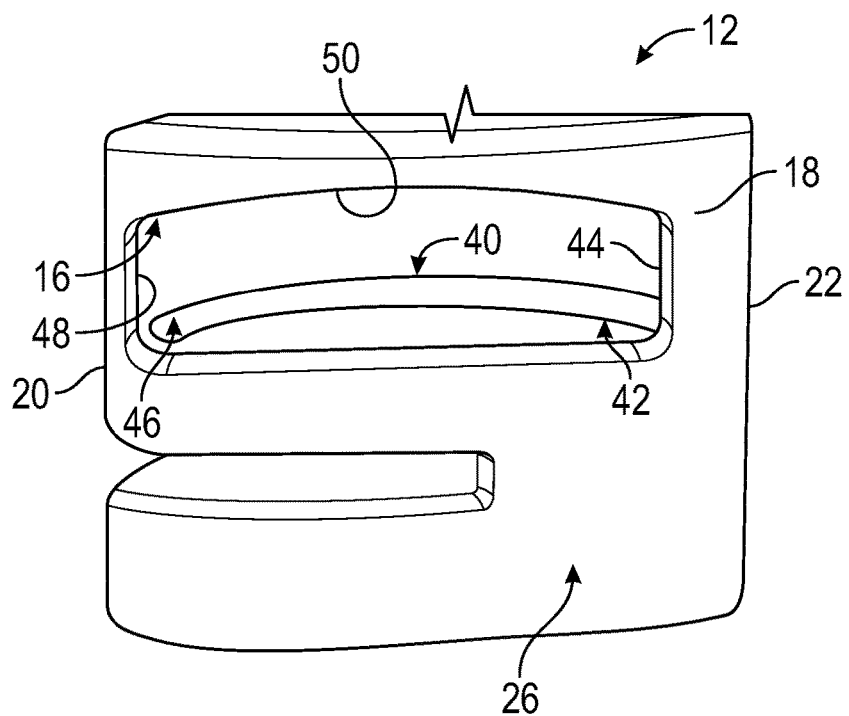
FIG. 4 is an end view of the tibial cutting block of FIG. 2.
Figure 5:
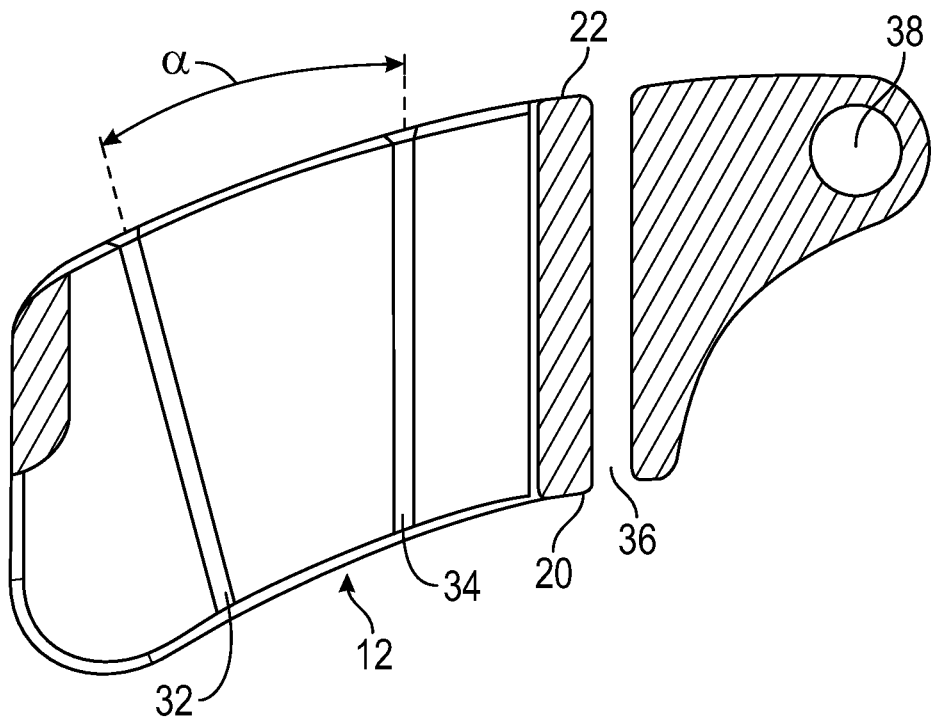
FIG. 5 is a cross-sectional view through section 5-5 of FIG. 2.
Figure 6:
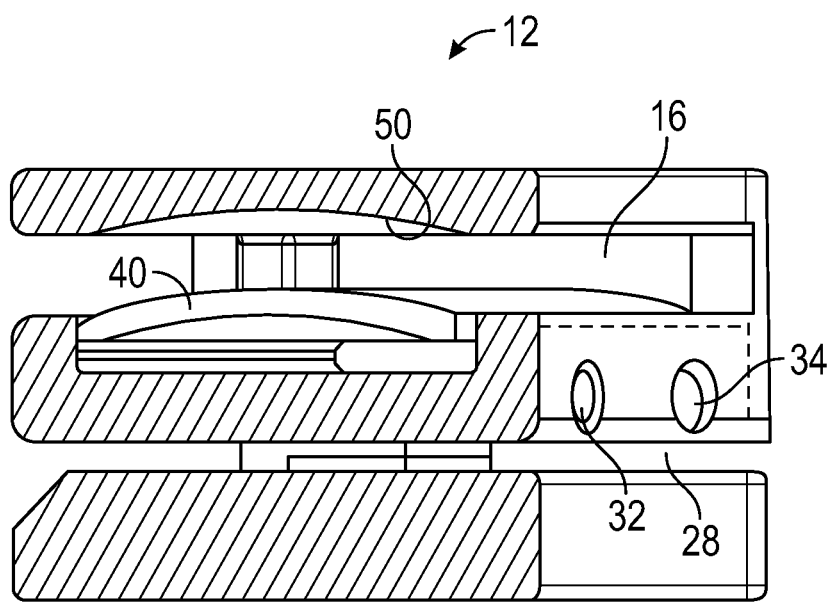
FIG. 6 is a cross-sectional view through section 6-6 of FIG. 2.

As best shown in FIGS. 4 and 6, a biasing clip 40 may be integrally formed as part of the block body 18. In an embodiment, the biasing clip 40 establishes a floor of the pin receiving slot 16. The biasing clip 40 may include a cantilevered design in which a first end portion 42 is integrally formed with an inner wall 44 of the front side 22 of the block body 18, and a second end portion 46 extends adjacent to an inner wall 48 of the tibial attachment side 20 but is unattached thereto. The biasing clip 40 may include an arced curvature between the first and second end portions 42, 46. Due at least in part to the cantilevered design and the arced curvature, the biasing clip 40 may induce a biasing force for biasing the slope setting pin 14 toward a surface of the block body 18, thereby firmly securing the slope setting pin 14 within the pin receiving slot 16 while still allowing for movement and adjustability (e.g., internal/external rotation) of the tibial cutting block 12 relative to the slope setting pin 14. In an embodiment, the biasing clip 40 biases the slope setting pin 14 against an upper wall 50 that delineates an upper portion of the pin receiving slot 16.

The tibial cutting block 12 may be an additionally manufactured part made of a polymeric material (e.g., nylon). However, other manufacturing techniques and materials could be utilized to construct the tibial cutting block 12 within the scope of this disclosure.

Dependent, for example, on which section of the tibia requires cuts and whether the left or the right tibia need treated, the tibia cutting block could look like the tibial cutting block 12 of FIGS. 2-6. The tibial cutting block could also have reversed left and right sides, whereas, for example, the first fixation pin hole 32 would be oriented at the right side of the block body 18, and the second cutting slot 30 and the third fixation pin hole 36 would be oriented at the left side of the block body 18.

Figure 7:
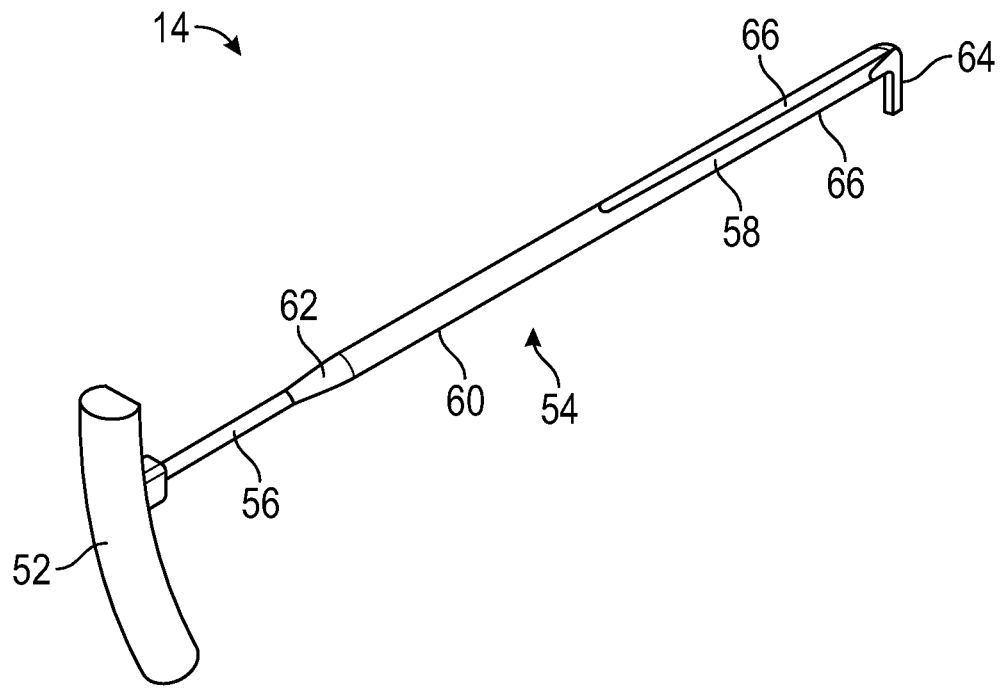
FIG. 7 is a perspective view of a slope setting pin of the tibial cutting guide assembly of FIG. 1.
Figure 8:
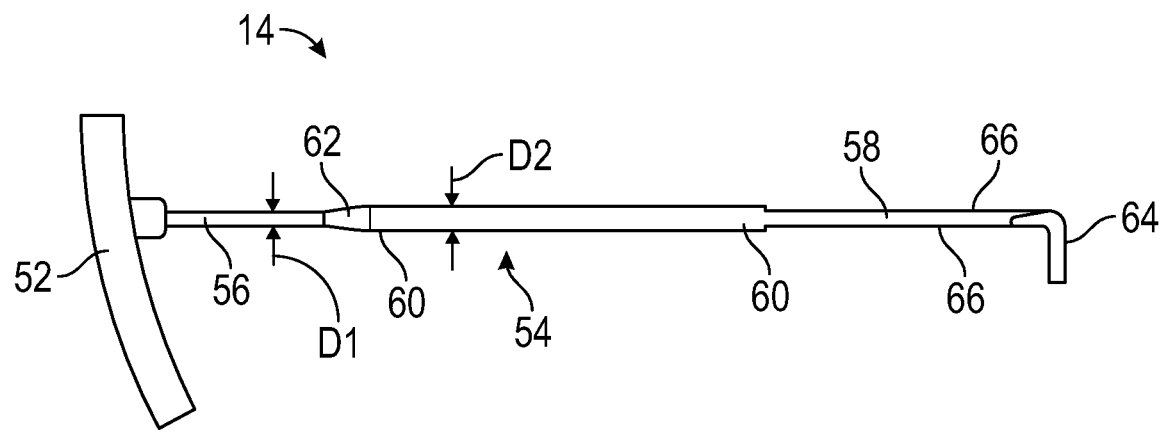
FIG. 8 is a front view of the slope setting pin of FIG. 7.

The slope setting pin 14 of the tibial cutting guide assembly of FIG. 1 is further illustrated with reference to FIGS. 7-8. The slope setting pin 14 may include a handle 52 and an elongated shaft 54 that extends along a longitudinal axis away from the handle 52.

The handle 52 of the slope setting pin 14 may be a curved handle. In an embodiment, the curvature of the handle 52 matches the curvature of the front side 22 of the tibial cutting block 12. Together, the tibial cutting block 12 and the handle 52 may establish a gripping portion for ergonomically handling the tibial cutting guide assembly 10 during use.

The elongated shaft 54 of the slope setting pin 14 may include a proximal section 56, a distal section 58, and a mid-section 60 between the proximal section 56 and the distal section 58. The proximal section 56 may connect at one end to the handle 52 and at an opposite end to the mid-section 60 via a tapering portion 62. The proximal section 56 may include a first diameter D1 that is smaller than a second diameter D2 of the mid-section 60. As further discussed below, the smaller first diameter D1 of the proximal section 56 allows the elongated shaft 54 to be bent in order to reposition the slope setting pin 14 out of the path of other instruments that may need to be inserted through the tibial cutting block 12.

The diameter D1 of the proximal section 56 of the elongated shaft 54 may be configured such that the biasing clip 40 cannot bias the slope setting pin 14 toward the upper wall 50 when the proximal section 56 is positioned in the first cutting slot 28. The slope setting pin 14 is therefore more freely movable relative to the tibial cutting block 12 when the proximal section 56 is positioned in the first cutting slot 28. In addition, the diameter D2 of the mid-section 60 of the elongated shaft 54 may be configured such that the slope setting pin 14 is biased by the biasing clip 40 when the mid-section 56 is positioned in the first cutting slot 28. The slope setting pin 14 is therefore less freely movable relative to the tibial cutting block 12 when the mid-section 60 is positioned in the first cutting slot 28. The ability to adjust the firmness of the engagement of the slope setting pin 14 relative to the tibial cutting block 12 enables numerous advantages, including but not limited to the ability to handle and maneuver the tibial cutting guide assembly 10 using only one hand.

The distal section 58 of the elongated shaft 54 may include a hook-shaped tip 64 at its end. The hook-shaped tip 64 may be inserted into the joint space between the femur and the tibia and then be rotated for securing the slope setting pin 14 relative to the tibia.

The distal section 58 of the elongated shaft 54 may additionally include a pair of flat surfaces 66. The flat surfaces 66 help keep the slope setting pin 14 from sliding medially or laterally with respect to the femoral bone once the slope setting pin 14 is inserted into the joint space between the femur and the tibia.

FIGS. 9-19, with continued reference to FIGS. 1-8, schematically illustrate an exemplary method for preparing a tibia 68 for receiving an arthroplasty implant. The method may be performed as part of an arthroplasty procedure. The unique design of the tibial cutting guide assembly 10 assists with tibial resection by providing patient specific tibial slope and level resectioning while providing for surgical control over internal/external rotation and varus/valgus alignment. Fewer or additional steps than are recited below could be performed within the scope of this disclosure, and the recited order of steps depicted in FIGS. 9-19 is not intended to limit this disclosure.

Figure 9:
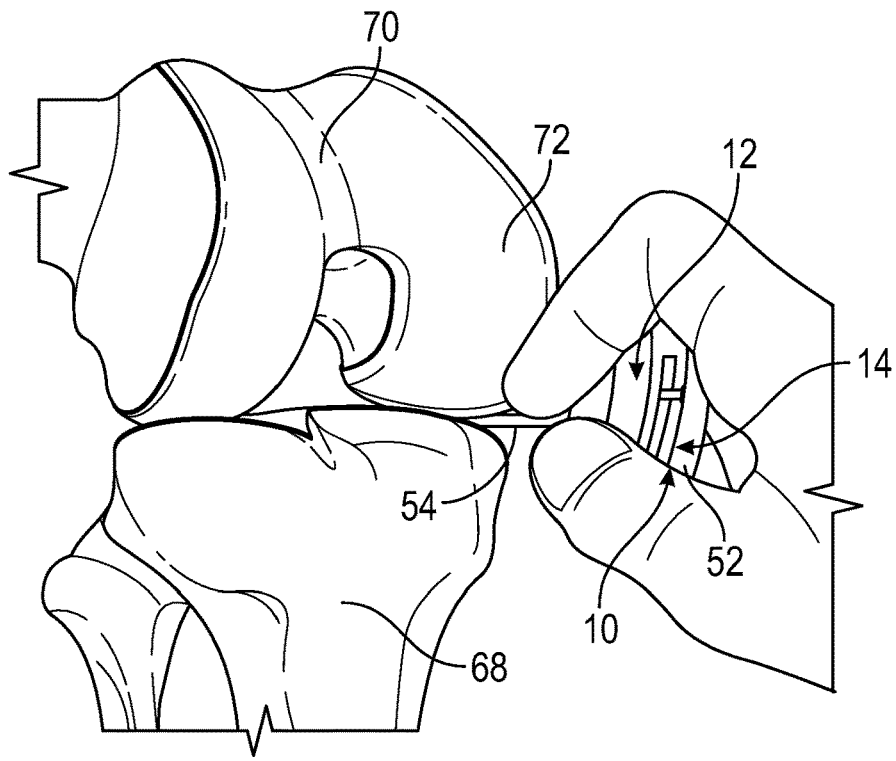
FIGS. 9, 10, 11, 12, 13, 14, 15, 16, 17, 18, and 19 schematically illustrate an exemplary method for preparing a bone for receiving an arthroplasty implant.

Referring first to FIG. 9, while holding the side appropriate tibial cutting block 12 in the surgeon's hand as an extension of the handle 52 of the slope setting pin 14, the elongated shaft 54 of the slope setting pin 14 may be inserted into the joint space between a patient's femur 70 and the tibia 68. The elongated shaft 54 may be inserted at about the mid-line of one of the femoral condyles 72 (in the illustrated embodiment, the femoral condyle 72 is the medial condyle of a right knee). The slope setting pin 14 may then be rotated about 90 degrees in order to position the hook-shaped tip 64 against a posterior surface 74 of the tibia 68 (see FIG. 19). When properly inserted, the slope setting pin 14 stabilizes the tibial cutting block 12 relative to the tibia 68 and also defines a native tibial slope as referenced by the anterior and posterior aspects of the tibia 68. The slope setting pin 14 further establishes an appropriate tibial resection level by creating space (e.g., approximately 9 mm) from the posterior femur to the tibial resection.

Figure 10:
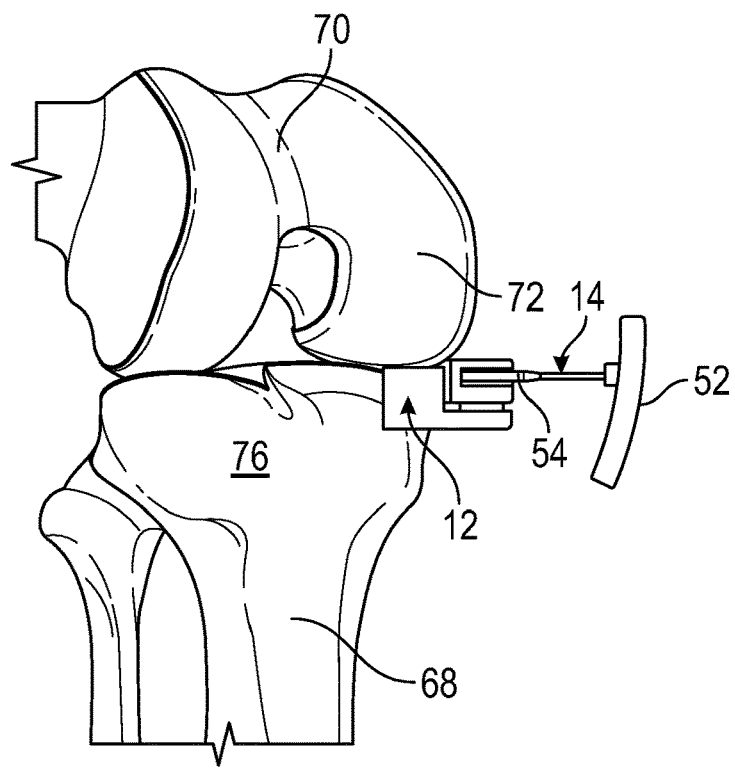

Next, as shown in FIG. 10, the tibial cutting block 12 may be moved into contact with an anterior surface 76 of the tibia 68. For example, the tibial cutting block 12 may be slid along the elongated shaft 54 of the slope setting pin 14 toward the anterior surface 76 and may also be rotated towards the midline of the tibia 68.

Figure 11:
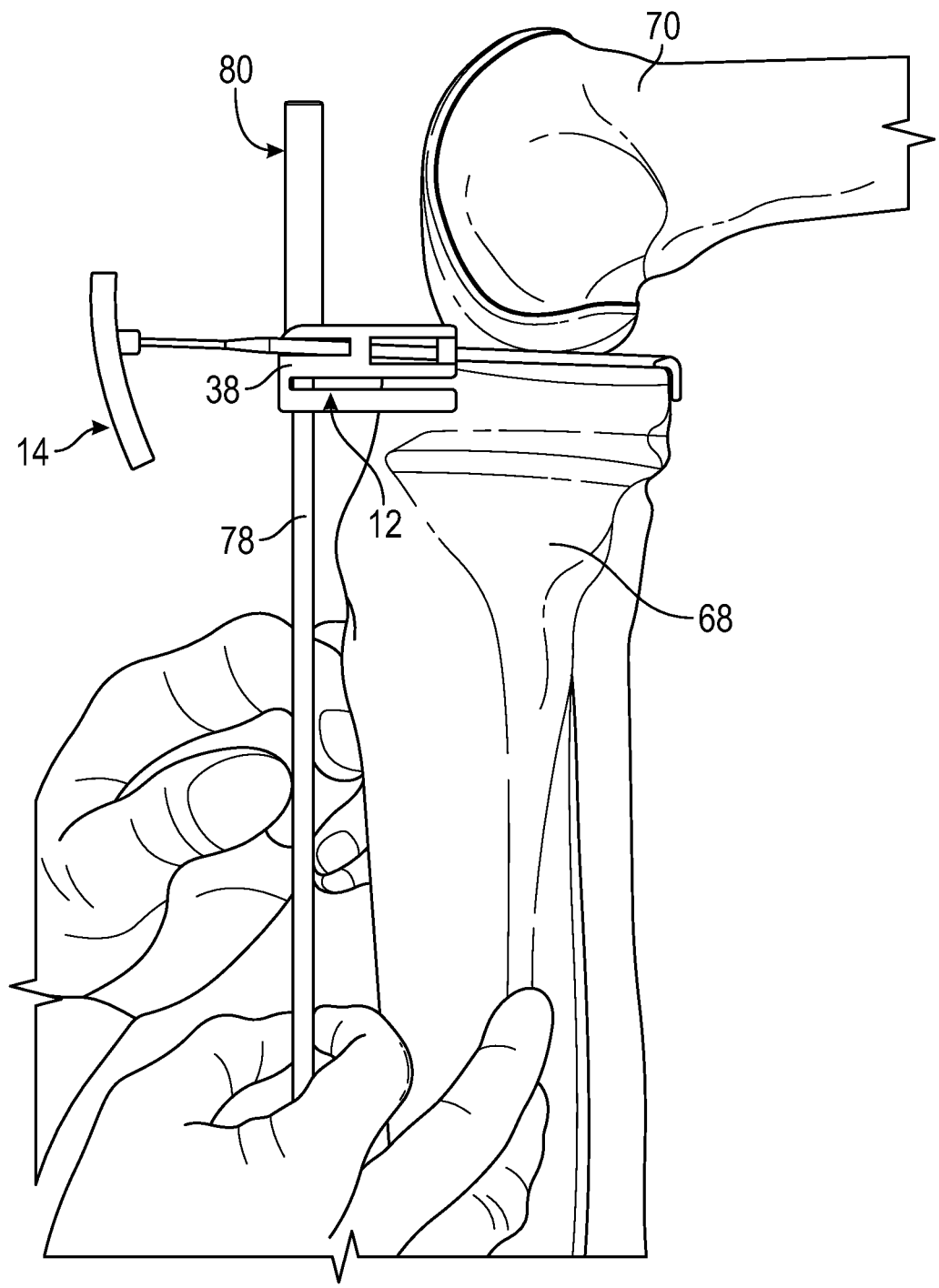

Once the tibial cutting block 12 is positioned as desired, a drop rod 78 of a varus-valgus alignment guide 80 may be inserted through the alignment rod hole 38 of the tibial cutting block 12 (see FIG. 11). The drop rod 78 may then be utilized for achieving appropriate varus-valgus alignment of the tibial cutting block 12 relative to the tibia 68.

Figure 12:
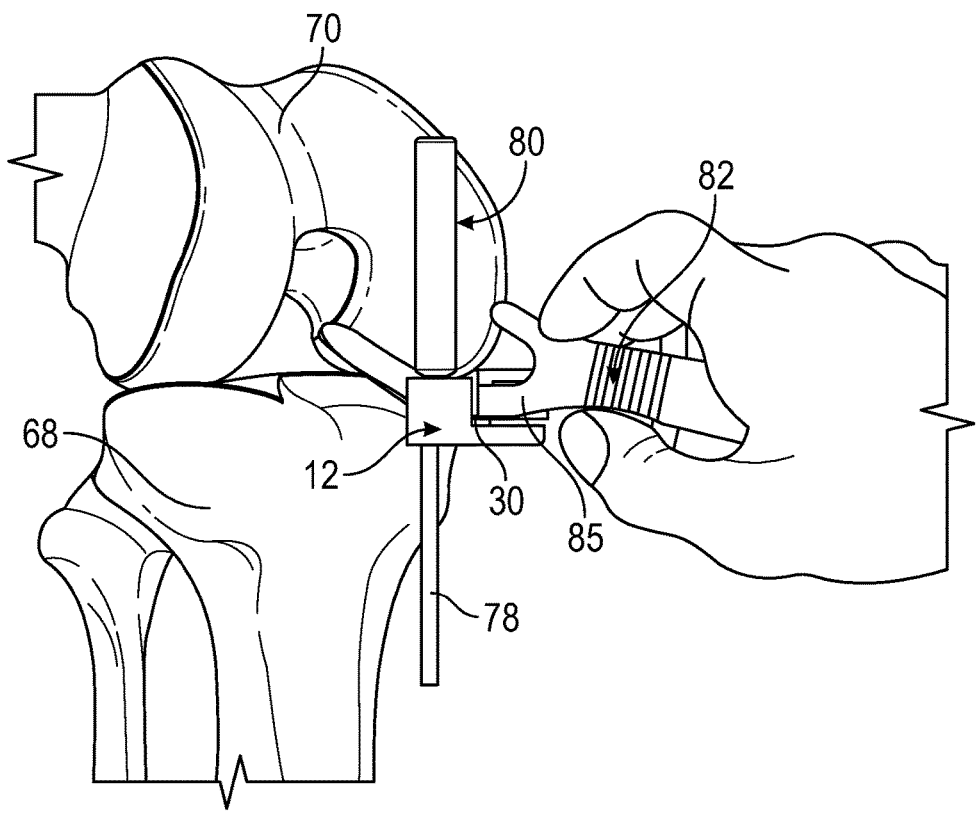

An angel wing tool 82 may optionally be utilized to ensure appropriate internal/external rotation and medial/lateral positioning of the tibial cutting block 12, and more particularly the first and second cutting slots 28, 30, relative to the tibia 68 (see FIG. 12). A prong 85 of the angel wing tool 82 may be inserted through the second cutting slot 30 for adjusting the internal/external rotation of the second cutting slot 30, and thus a vertical cutting path of the tibial cutting block 12, relative to the tibia 68.

Figure 13:
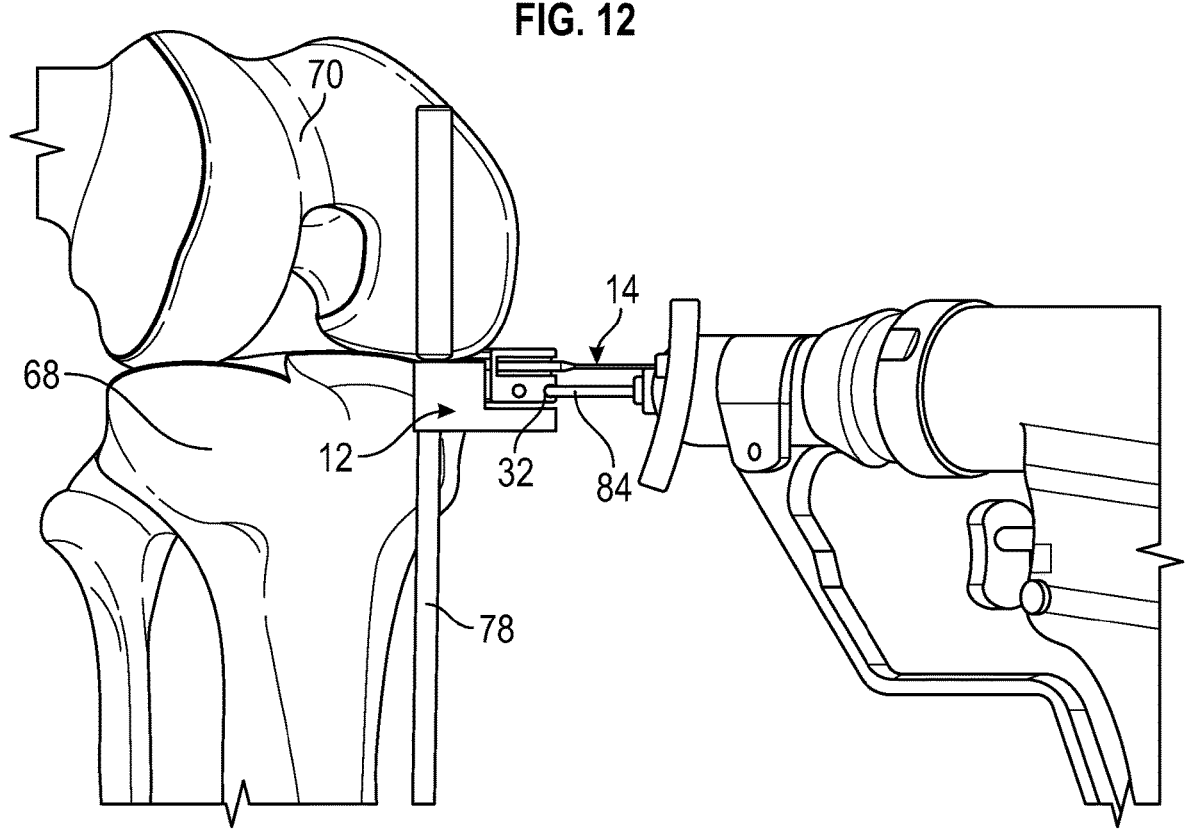
Figure 14:
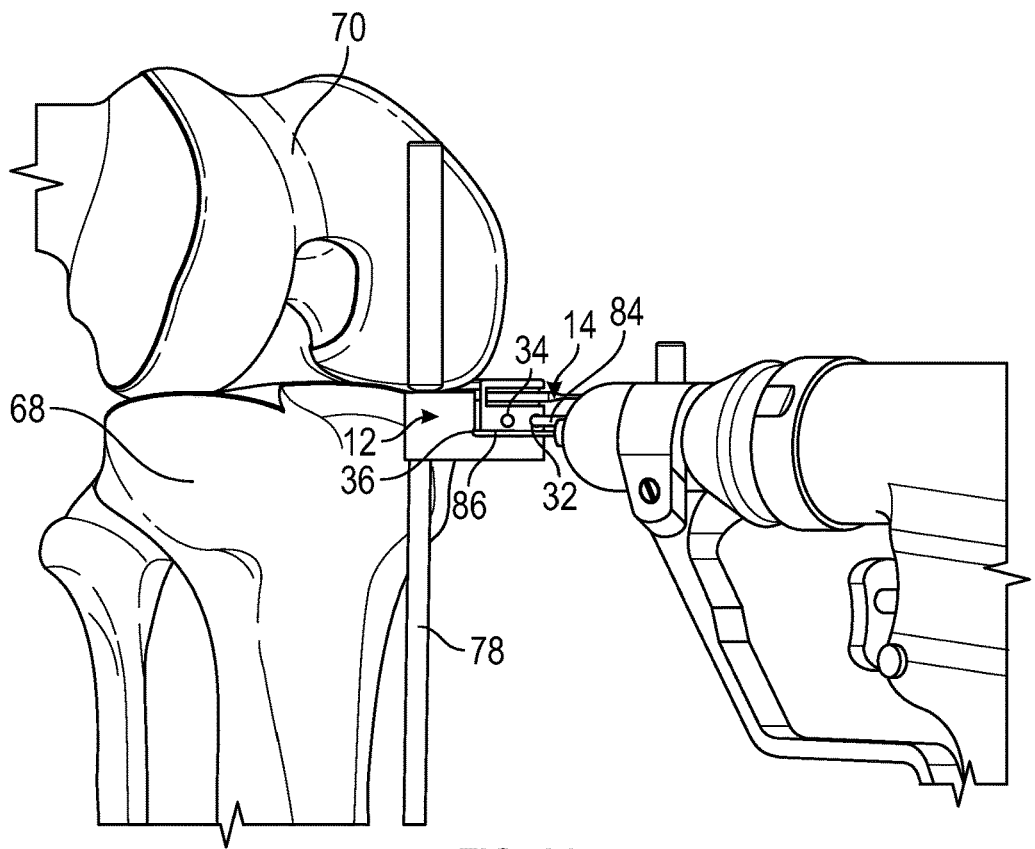

Referring now to FIGS. 13 and 14, the method may proceed by inserting a fixation pin in the most accessible fixation pin holes of the tibial cutting block 12. In an embodiment, one fixation pin 84 is inserted through the second fixation pin hole 34 (see FIG. 13), and another fixation pin 86 is inserted through the third fixation pin hole 36 of the tibial cutting block 12 (see FIG. 14). However, the order of insertion and insertion location of the fixation pins 84, 86 are not intended to limit this disclosure.

Figure 15:
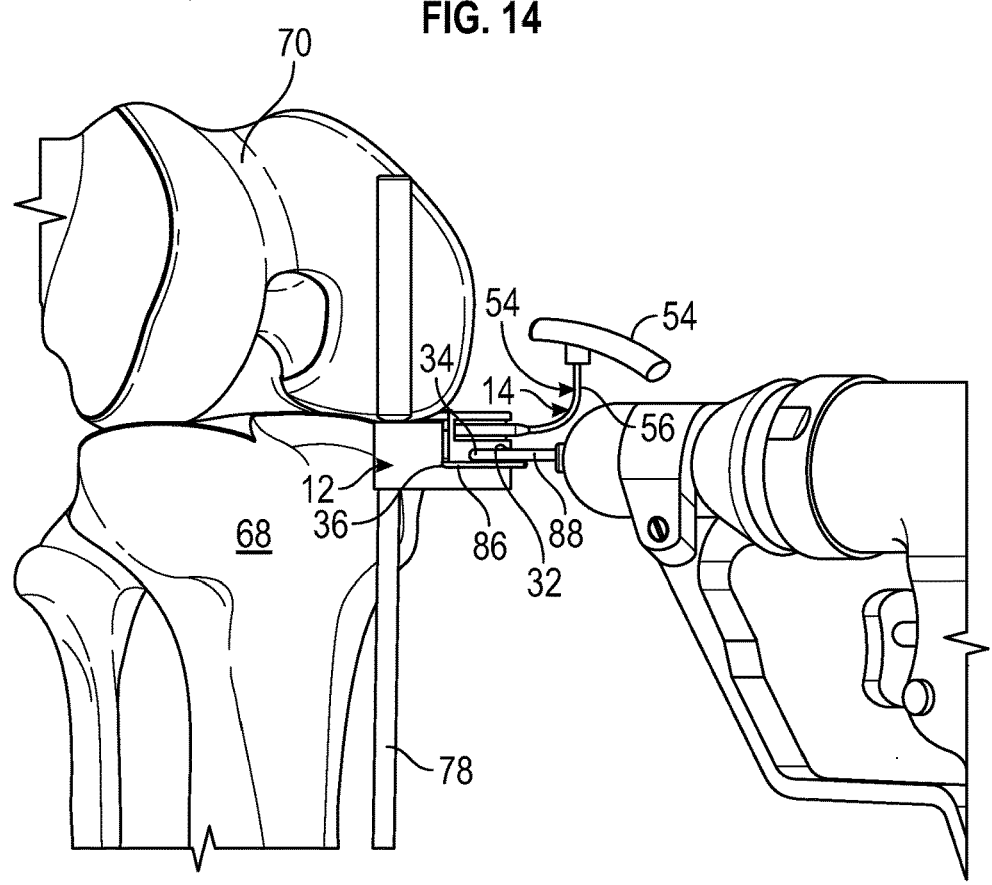
Figure 16:
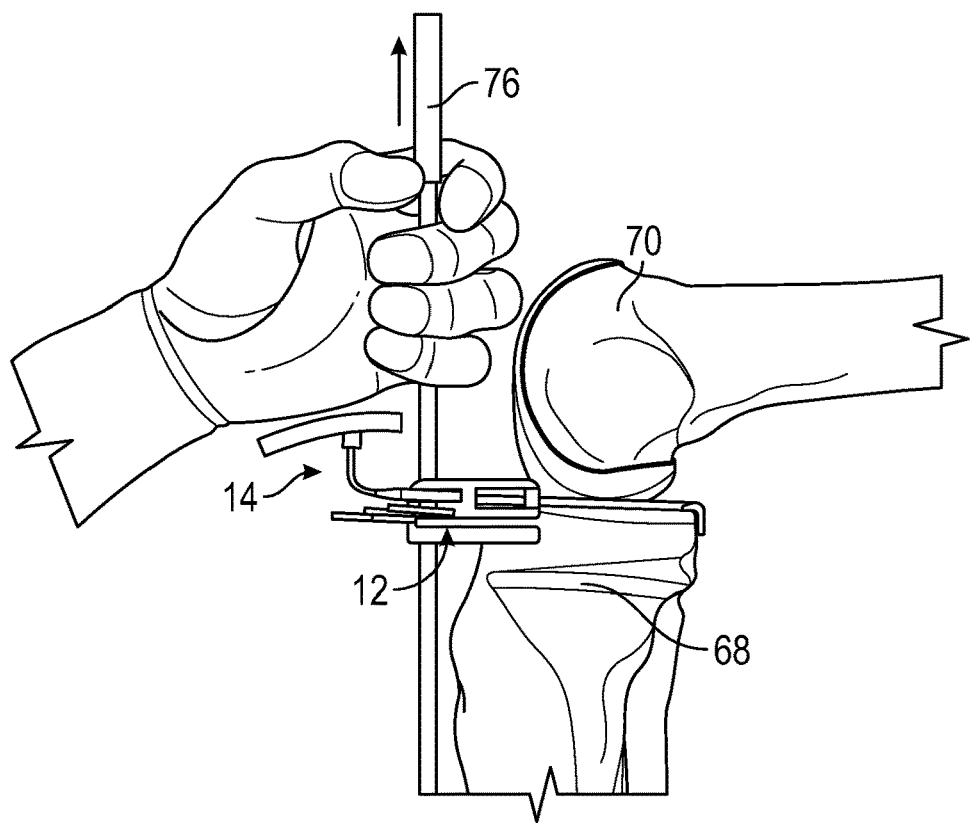

Once satisfactory alignment of the tibial cutting block 12 has been achieved, the proximal section 56 of the elongated shaft 54 of the slope setting pin 14 may be bent in order to bend the handle 52 of the slope setting pin 14 upwardly away from the tibial cutting block 12 (see FIG. 15). An additional fixation pin 88 may then be inserted through the second fixation pin hole 34 (or any other fixation pin hole that has not yet been used). If still in place, the drop rod 78 and the angel wing tool 82 may be removed from the tibial cutting block 12 (see FIG. 16).

Figure 17:
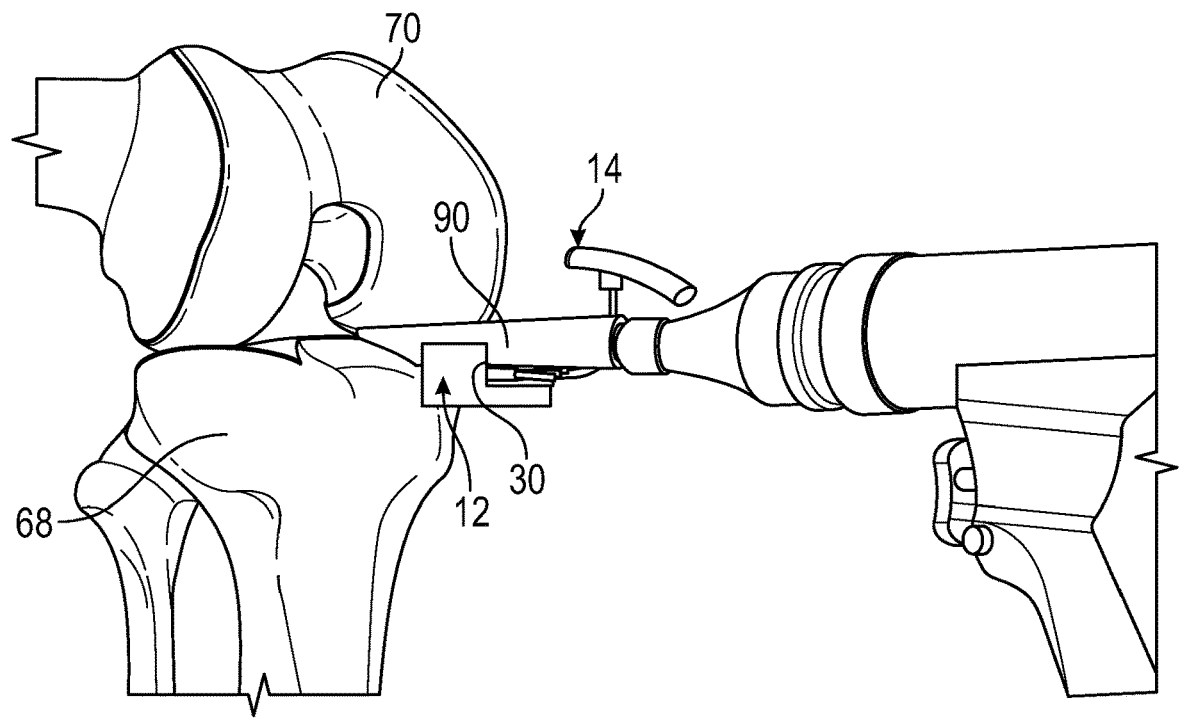
Figure 18:
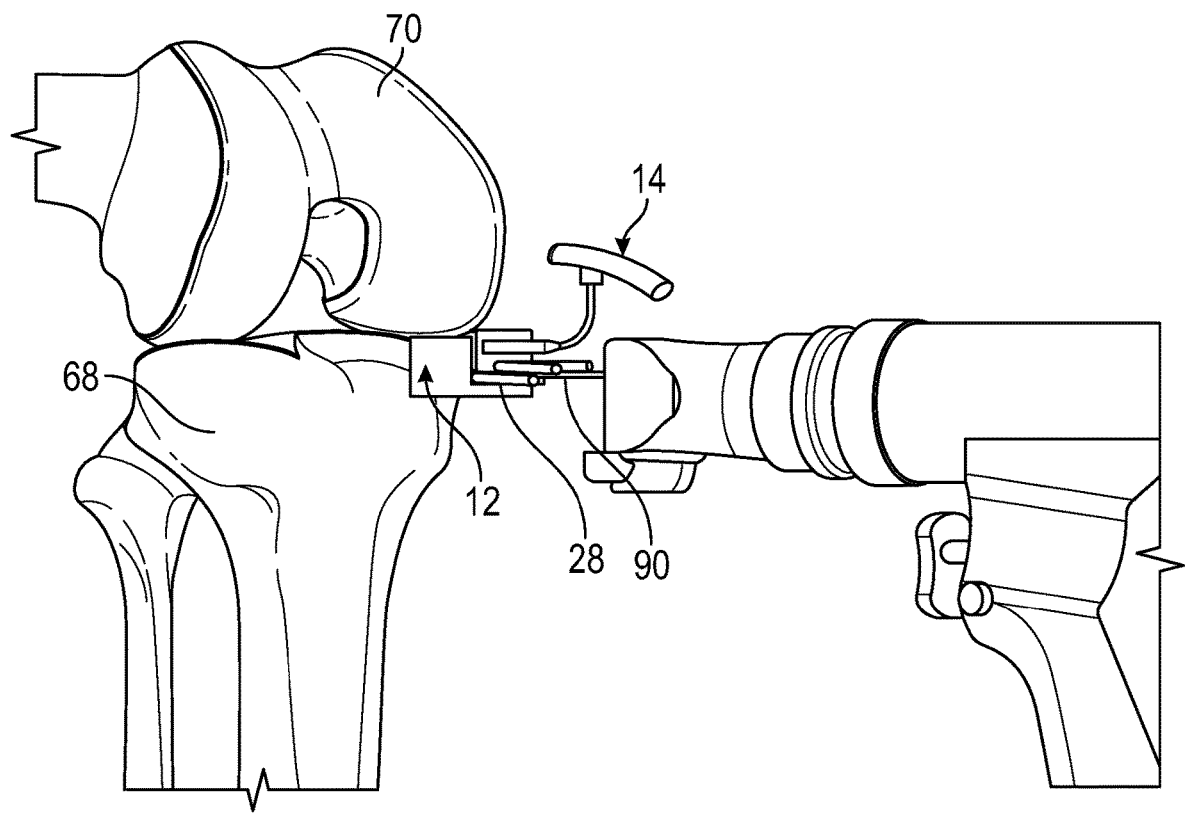
Figure 19:
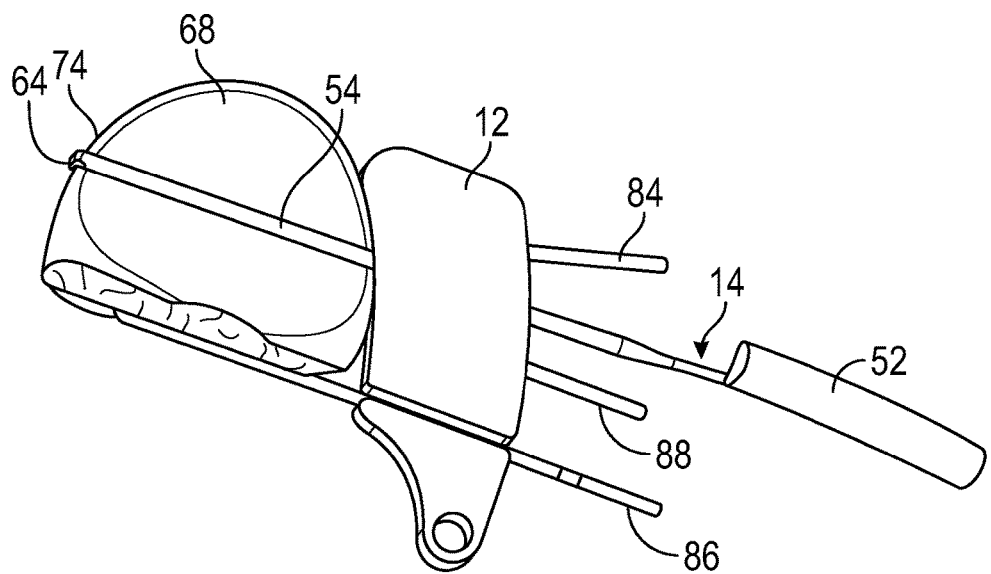

Referring now to FIGS. 17 and 18, vertical and horizontal resections can next be made in the tibia 68 by inserting a saw blade 90 or other cutting tool through the first and second cutting slots 28, 30 of the tibial cutting block 12. The order of making the cuts is not intended to limit this disclosure and could vary from surgery to surgery. The fixation pins 86, 88 may act as a secondary guide for defining the cutting plane of the saw blade 90 when making the horizontal resections through the first cutting slot 28.

Once a complete resection has been performed, the hook-shaped tip 64 of the slope setting pin 14 and the fixation pins 84, 86, 88 may be utilized to facilitate removal of the resected portions of the tibial bone. Once all cuts are made and the resected portions removed, the arthroplasty procedure can proceed to any additional steps necessary for preparing the joint for receiving one or more arthroplasty implants.

As alluded to above, the tibial cutting guide assembly 10 may be part of an arthroplasty instrument set. For example, the tibial cutting guide assembly 10 could be packaged together as a kit with other surgical instruments, such as the varus-valgus alignment guide 80, the angle wing tool 82, the fixation pins 84-88, etc., for formulating the arthroplasty instrument set.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A tibial cutting guide assembly, comprising:
a tibial cutting block including a biasing clip; and
a slope setting pin biased toward a surface of the tibial cutting block by the biasing clip.

2. The tibial cutting guide assembly as recited in claim 1, wherein the slope setting pin is adjustably received within a pin receiving slot of the tibial cutting block.

3. The tibial cutting guide assembly as recited in claim 2, wherein the surface is an upper wall of a block body of the tibial cutting block that delineates a portion of the pin receiving slot.

4. The tibial cutting guide assembly as recited in claim 1, wherein a block body of the tibial cutting block includes a unitary, monoblock design and is comprised of a polymeric material.

5. The tibial cutting guide assembly as recited in claim 1, wherein the tibial cutting block includes a first cutting slot and a second cutting slot that is separated from the first cutting slot by an interior wall of the tibial cutting block.

6. The tibial cutting guide assembly as recited in claim 5, wherein a first fixation pin hole and a second fixation pin hole extend through the tibial cutting block and open into the first cutting slot.

7. The tibial cutting guide assembly as recited in claim 6, wherein a third fixation pin hole extends through the tibial cutting block and opens into the second cutting slot.

8. The tibial cutting guide assembly as recited in claim 1, wherein the biasing clip includes a first end portion integrally formed with an inner wall of a front side of the tibial cutting block, a second end portion arranged adjacent to an inner wall of a tibial attachment side of the tibial cutting block, and an arced curvature between the first end portion and the second end portion.

9. The tibial cutting guide assembly as recited in claim 1, wherein the biasing clip establishes a floor of a pin receiving slot of the tibial cutting block, and further wherein the slope setting pin is movably received within the pin receiving slot.

10. The tibial cutting guide assembly as recited in claim 1, wherein the slope setting pin includes an elongated shaft comprising a distal section portion that includes a hook-shaped tip and a pair of flat surfaces.

11. The tibial cutting guide assembly as recited in claim 1, wherein the slope setting pin includes an elongated shaft comprising a proximal section, a distal section, and a mid-section, and further wherein the proximal section includes a first diameter that is smaller than a second diameter of the mid-section.

12. An arthroplasty instrument set, comprising:
the tibial cutting block assembly of claim 1;
a varus-valgus alignment device; and
at least two fixation pins.

* * * * *